United States Patent
Debon et al.

(10) Patent No.: US 11,096,884 B2
(45) Date of Patent: Aug. 24, 2021

(54) COMPOSITION CONTAINING OLEOSOMES OF DIFFERENT SIZE DISTRIBUTION

(71) Applicant: CARGILL, INCORPORATED, Wayzata, MN (US)

(72) Inventors: Stéphane Jules Jérome Debon, Vilvoorde (BE); Katlijn Rene Nicolette Moelants, Vilvoorde (BE); Lucía de la Concepción Cabas Rodriguez, Antwerp (BE); Gustav Maximilian Waschatko, Vilvoorde (BE)

(73) Assignee: Cargill, Incorporated, Wayzata, MN (US)

( * ) Notice: Subject to any disclaimer, the term of this patent is extended or adjusted under 35 U.S.C. 154(b) by 339 days.

(21) Appl. No.: 15/768,233

(22) PCT Filed: Oct. 14, 2016

(86) PCT No.: PCT/US2016/057040
§ 371 (c)(1),
(2) Date: Apr. 13, 2018

(87) PCT Pub. No.: WO2017/066569
PCT Pub. Date: Apr. 20, 2017

(65) Prior Publication Data
US 2020/0237641 A1 Jul. 30, 2020

(30) Foreign Application Priority Data

Oct. 15, 2015 (EP) .................................. 15189993

(51) Int. Cl.
| A61K 8/92 | (2006.01) |
|---|---|
| A23L 33/105 | (2016.01) |
| C12G 3/055 | (2019.01) |
| A23D 7/00 | (2006.01) |
| A61K 8/06 | (2006.01) |
| A61K 8/14 | (2006.01) |
| A61K 9/107 | (2006.01) |
| A61K 47/44 | (2017.01) |
| A61Q 19/00 | (2006.01) |
| C12G 3/06 | (2006.01) |

(52) U.S. Cl.
CPC .............. *A61K 8/922* (2013.01); *A23D 7/001* (2013.01); *A23L 33/105* (2016.08); *A61K 8/062* (2013.01); *A61K 8/064* (2013.01); *A61K 8/14* (2013.01); *A61K 9/107* (2013.01); *A61K 47/44* (2013.01); *A61Q 19/00* (2013.01); *C12G 3/055* (2019.02); *C12G 3/06* (2013.01); *A23V 2002/00* (2013.01); *A61K 2800/10* (2013.01); *A61K 2800/412* (2013.01); *A61K 2800/5922* (2013.01)

(58) Field of Classification Search
CPC ........ A61K 8/922; A61K 8/062; A61K 8/064; A61K 8/14; A61K 9/107; A61K 47/44; A61K 2800/10; A61K 2800/412; A61K 2800/5922; A61Q 19/00; A23L 33/105; C12G 3/055; C12G 3/06; A23D 7/001; A23V 2002/00
See application file for complete search history.

(56) References Cited

U.S. PATENT DOCUMENTS

| | | | |
|---|---|---|---|
| 3,971,856 A | 7/1976 | Daftary | |
| 4,025,658 A | 5/1977 | Pominski | |
| 4,362,759 A | 12/1982 | Harris | |
| 5,599,513 A | 2/1997 | Masaki | |
| 5,613,583 A | 3/1997 | Kono | |
| 5,683,740 A | 11/1997 | Voultoury | |
| 6,183,762 B1 | 2/2001 | Deckers | |
| 2009/0175808 A1 | 7/2009 | Galley et al. | |
| 2009/0280079 A1 | 11/2009 | Gray | |
| 2009/0311410 A1 * | 12/2009 | Burling | A23C 9/1307 426/603 |
| 2013/0258801 A1 * | 10/2013 | Almeida Rivera | B01F 7/00816 366/337 |

FOREIGN PATENT DOCUMENTS

| | | |
|---|---|---|
| EP | 0680751 A1 | 11/1995 |
| EP | 1007554 B1 | 3/2006 |
| EP | 1952695 A1 | 8/2008 |
| EP | 1765279 B1 | 11/2010 |
| EP | 2442779 B1 | 11/2013 |
| WO | 9827115 A1 | 6/1998 |
| WO | 9853698 A1 | 12/1998 |
| WO | 2000030602 W | 6/2000 |
| WO | 2005030169 W | 4/2005 |
| WO | 2009126301 W | 10/2009 |
| WO | 2009126302 W | 10/2009 |
| WO | 2012110797 W | 8/2012 |
| WO | 2013152340 A1 | 10/2013 |
| WO | WO 2013152340 A1 * | 10/2013 |
| WO | 2014154780 W | 10/2014 |

OTHER PUBLICATIONS

Tzen et al. "Lipids, Proteins, and structure of Seed Oil Bodies from Diverse Species" in Plant Physiology (1993) 101:267-276.*
Huang, et al., "Oil Bodies and Oleosins in Seeds", Annual Review of Plant Physiology and Plant Molecular Biology, Annual Reviews Inc, US, vol. 43, Jan. 1, 1992, p. 179.
Nikiforidis, Constantinos V, et al., "Rheological characteristics and physicochemical stability of dressing-type emulsions made of oil bodies—egg yolk blends", Food Chemistry, Elsevier Ltd, NL, vol. 134 (1), Feb. 9, 2012, 64-73.
Tzen J T C, et al., "Lipids, Proteins, and Structure of Seed Oil Bodies from Diverse Species", Plant Physiol. 101(1), Jan. 1993, 267-276.

(Continued)

*Primary Examiner* — Blessing M Fubara

(57) ABSTRACT

The present invention relates to a composition containing first oleosomes having a first distribution D50(1) and second oleosomes having a second size distribution D50(2).

20 Claims, 6 Drawing Sheets

(56) References Cited

OTHER PUBLICATIONS

White D A, et al., "Sunflower-seed oil body emulsions: Rheology and stability assessment of a natural emulsion", Food Hydrocolloids, Elsevier BV, NL vol. 22(7), Oct. 1, 2008, 1224-1232.

Aguilar et al., "Rheological behavior of processed mustard. I: effect of milling treatment," 1990, journal of Texture studies 22:59-84.

Isolation and Physiochemical Characterization of the Half-Unit Membranes of Oilseed Lipid Bodies, T.J. Jacks, et al., JAOCS, vol. 67, No. 6 (Jun. 1990).

Kumar, N. S. K. et al., A Fresh Look at Coconut and its Processing, INFORM, Nov. 1995, vol. 6, No. 11, pp. 1217-1218, 1220-1222.

Lawhon et al., The processing and storage characteristics of glandless cottonseed, 1966, J. Am. Oil, Chem, Soc. 63:533-534.

Leber, R. et al., "Characterization of lipid particles of the yeast, *Saccharomyces cerevisiae*" 1994, Yeast 10: 1421-1428.

Murphy, D. J. and Cummins I., "Seed oil-bodies: isolation, composition and role of oil-body apolipoproteins" 1989, Phytochemistry, 28: 2063-2069.

Pieper-Fürst et al., "Purification and Characterization of a 14-Kilodalton Protein That Is Bound to the Surface of Polyhydroxyalkanoic Acid Granules in Rhodococcus ruber" 1994, J. Bacteriol.176: 4328.

Roessler, P.G., "Effects of Silicon Deficiency on Lipid Composition and Metabolism in the Diatom Cyclotella Cryptica" 1988, J. Physiol. (London), 24: 394-400.

Ting, J. T. et al., "Oleosin of Plant Seed Oil Bodies Is Correctly Targeted to the Lipid Bodies in Transformed Yeast," 1997, J. Biol Chem.272: 3699-3706.

\* cited by examiner

COMPOSITION CONTAINING OLEOSOMES OF DIFFERENT SIZE DISTRIBUTION

CROSS-REFERENCE TO RELATED APPLICATIONS

This application is a national phase application of International Application PCT/US2016/057040, filed 14 Oct. 2016, entitled "COMPOSITION CONTAINING OLEOSOMES OF DIFFERENT SIZE DISTRIBUTION," which claims the benefit of European Patent Application Serial No. 15189993.7 filed 15 Oct. 2015, entitled "COMPOSITION CONTAINING OLEOSOMES OF DIFFERENT SIZE DISTRIBUTION," both of which applications are hereby incorporated by reference herein in their entirety.

FIELD OF THE INVENTION

The present invention relates to a composition containing oleosomes and its applications thereof, in particular in food, pharmaceutical and personal care products.

BACKGROUND OF THE INVENTION

Oleosomes, also known as "oil bodies", "lipid bodies", "lipid droplets" or "spherosomes", are pre-emulsified droplets or vesicles of oil stored in plant seeds and used as energy source for plant growth and metabolism. The droplets are stabilised by a layer containing phospholipids and various proteins associated with the oleosomes generically called "intrinsic proteins", said intrinsic proteins containing mostly oleosins. The oleosins contain a hydrophilic part, which is present at the oleosome's surface and a hydrophobic part which is anchored in the oil and ensures for oleosome stability. The oil contained by the oleosomes contains a mixture of triglycerides of which the exact composition depends on the plant species from which the oil is derived. It has become possible though through a combination of classical breeding and genetic engineering techniques to manipulate the oil profile of seeds and expand on the naturally available repertoire of plant oil compositions.

Oleosomes are typically extracted from seeds by a process containing grinding the seeds, washing, filtering and homogenising the ground seeds to form an aqueous suspension and centrifuging said suspension to separate the oleosomes. The separated oleosomes are skimmed and recovered and eventually washed or purified to remove non-oleosome associated proteins (generically called "extrinsic proteins"), allergens, undesirable odours, flavours, colours and other unwanted contaminants. Such processes are known for example from U.S. Pat. No. 5,683,740; U.S. Pat. No. 5,613,583; WO98/53698; WO2000/30602; WO 2005/030169; WO 2009/126301; EP 1 007 554; and EP 1 952 695.

The extracted and washed oleosomes are typically spherical particles with typical diameters of at least 0.1 µm depending on the plant species of origin. For rapeseed for example, the specific value was about 0.7 µm. When carefully handled, it was found that washed oleosomes can be obtained having a unimodal size distribution with sizes symmetrically distributed around a specific value depending on the plant species of origin. Having oleosomes symmetrically and unimodally distributed around a specific value seems to be beneficial when the oleosomes are used in the manufacturing of various products containing thereof. Moreover, oleosomes having increased surface-to-volume ratio showed various advantages during processing thereof, but also when formulated into applications e.g. they showed an optimized resistance against the various stresses applied thereon.

Washed and purified oleosomes are used typically in food, pharmaceutical and personal care products mainly for their excellent emulsification capacity. Emulsions, which are mixtures of two mutually insoluble components, the most known being water and oil, are widely used in formulations of various products. Commonly known domestic examples of emulsion-based formulations include mayonnaise, spreads, creamers, beverages, margarine and frozen desserts. Various other uses of oleosomes are known for example from U.S. Pat. No. 6,183,762; U.S. Pat. No. 5,599,513; EP 1 765 279; WO 2005/030169; WO 2009/126301; WO 2009/126302; WO 2014/154780; and EP 2 442 779 included herein by reference.

Although the oleosomes are providing products containing thereof with many advantageous properties, the present inventors discovered that their benefits are not fully leveraged. In particular, one would desire to incorporate increasing volumes of oleosomes per unit of volume of product in order to make a more efficient use thereof. However, this was not possible as products having a total oleosome-captured triglyceride content above 60 wt % per weight of the product were not manufactured hitherto.

Moreover, for specific products such as spreads, the rheological properties, e.g. shear thinning behavior and yield stress, at shear rates between 10 and 100 $sec^{-1}$ is important since their spreadability is correlated with said properties. The present inventors observed thus that the rheological properties of products containing oleosomes, in particular at shear rates between 10 and 100 $sec^{-1}$, can be optimized.

Also, the inventors observed that the rheological behavior and organoleptic properties of products containing oleosomes can be further optimized by more efficiently harnessing the benefits of oleosomes. In particular, there is a desire in the industry to provide compositions for manufacturing food, pharmacological and personal care products, said composition having a broader flavor spectrum, improved nutritional benefits, less dependence on botanical sources and/or optimized oxidation protection.

SUMMARY OF THE INVENTION

A need is therefore felt in the food industry for products containing oleosomes, which are optimally included therein but also utilized. In an attempt to respond to the industry need, the present invention provides a composition containing first oleosomes having a first size distribution D50(1) and second oleosomes having a second size distribution D50(2).

The present inventors surprisingly observed that the composition of the invention, hereinafter the inventive composition, had excellent usability delivering to products containing thereof excellent properties. The inventive composition was easily tunable to respond to even the most stringent requirements of products, e.g. rheological, nutritional, organoleptic and health requirements.

In particular, the inventive composition may optimally be included in products, e.g. food products or personal care products; for instance, a spread or a lotion containing thereof showed an optimum shear thinning behavior while having an increased amount of total oleosome-captured triglyceride (TOCT) content. By TOCT content is herein understood the amount of triglyceride inside the oil bodies contained per unit volume of product, e.g. spread or lotion.

It was also observed that other products such as baked products containing the inventive composition showed reduced oiling out in comparison with those made using standard recipes. Further benefits and advantages of the inventive composition will become apparent from the detailed description of the invention as presented hereinafter.

FIGURES

FIG. 1A (viscosity vs. shear rate) and FIG. 1B (G' vs. time) show the rheological behavior of the inventive composition when compared with compositions containing a single kind of oleosomes only.

DETAILED DESCRIPTION OF THE INVENTION

Figure 1A:
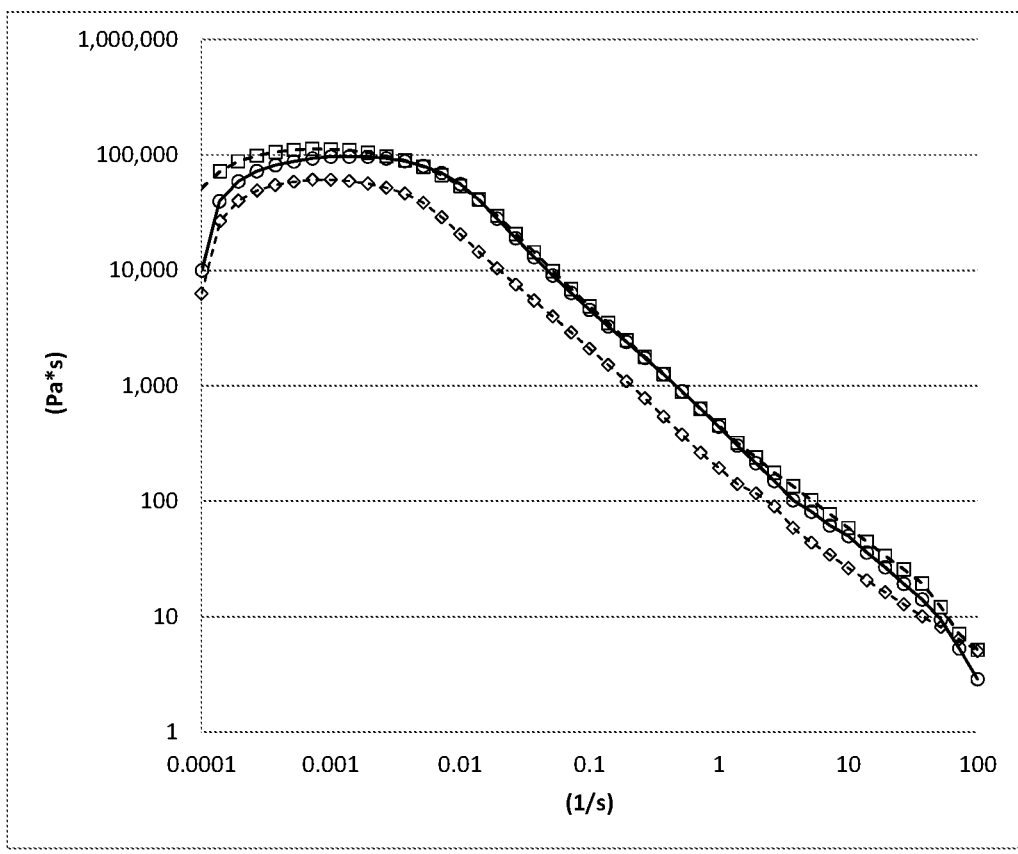

The present invention provides a composition containing first oleosomes having a first size distribution D50(1) and second oleosomes having a second size distribution D50(2). Preferably, D50(1) is smaller than D50(2), i.e. D50(1)<D50(2). In the inventive composition, the first oleosomes are mixed (or blended) with the second oleosomes, although enriched phases of first and/or second oleosomes may also be present therein.

Preferably, the inventive composition has a ratio D50(1)/D50(2) of at least 0.001, more preferably at least 0.01, most preferably at least 0.05. Preferably, the ratio D50(1)/D50(2) is at most 0.95, more preferably at most 0.75, most preferably at most 0.65. Preferably, the ratio D50(1)/D50(2) is between 0.001 and 0.95, more preferably between 0.01 and 0.75, even more preferably between 0.05 and 0.65.

In a preferred embodiment, the ratio D50(1)/D50(2) is between 0.001 and 0.95, more preferably between 0.01 and 0.90, even more preferably between 0.05 and 0.90, most preferably between 0.07 and 0.85.

Preferably, D50(1) is at least 120 nm, more preferably at least 150 nm, most preferably at least 180 nm. Preferably, D50(1) is at most 850 nm, more preferably at most 800 nm, most preferably at most 750 nm. In a preferred embodiment, D50(1) is between 150 nm and 850 nm, more preferably between 200 nm and 800 nm, most preferably between 250 nm and 750 nm.

Preferably, D50(2) is at least 500 nm, more preferably at least 550 nm, most preferably at least 600 nm. Preferably, D50(2) is at most 8000 nm, more preferably at most 7000 nm, most preferably at most 6000 nm. In a preferred embodiment, D50(2) is between 500 nm and 8000 nm, more preferably between 550 nm and 7000 nm, most preferably between 600 nm and 6000 nm.

In a preferred embodiment, D50(1) is at least 120 nm, more preferably at least 150 nm, most preferably at least 180 nm. Preferably, D50(1) is at most 550 nm, more preferably at most 450 nm, most preferably at most 400 nm. In a preferred embodiment, D50(1) is between 150 nm and 550 nm, more preferably between 200 nm and 550 nm, most preferably between 250 nm and 550 nm. For this particular embodiment, preferably, D50(2) is at least 500 nm, more preferably at least 550 nm, most preferably at least 600 nm. Preferably, D50(2) is at most 8000 nm, more preferably at most 7000 nm, most preferably at most 6000 nm. In a preferred embodiment, D50(2) is between 500 nm and 8000 nm, more preferably between 550 nm and 7000 nm, most preferably between 600 nm and 6000 nm.

In a preferred embodiment, D50(2) is at least 600 nm, more preferably at least 800 nm, most preferably at least 1000 nm. Preferably, D50(2) is at most 6000 nm, more preferably at most 4000 nm, most preferably at most 2500 nm. In a preferred embodiment, D50(2) is between 800 nm and 2500 nm, more preferably between 900 nm and 2200 nm, most preferably between 1000 nm and 2000 nm. For this particular embodiment, preferably, D50(1) is at least 120 nm, more preferably at least 150 nm, most preferably at least 180 nm. Preferably, D50(1) is at most 850 nm, more preferably at most 800 nm, most preferably at most 750 nm. In a preferred embodiment, D50(1) is between 150 nm and 850 nm, more preferably between 200 nm and 800 nm, most preferably between 250 nm and 750 nm.

The first and the second oleosomes are preferably extracted from different sources of origin. However, they can be also extracted from the same source of origin and subsequently processed to achieve the desired D50. For instance oleosomes naturally having a small D50, e.g. below 550 nm, can be coalesced, e.g. by heat, mechanically (by mixing, shearing and the like), by aeration and/or by germination, to create bigger oleosomes and hence obtaining higher D50s, e.g. above 600 nm. On the other hand oleosomes naturally having a large D50, e.g. above 600 nm, can be "broken" in smaller oleosomes e.g. by homogenization e.g. high pressure homogenization, to create smaller D50s, e.g. below 500 nm. Preferably, the D50 of the oleosomes used in the present invention is essentially the natural or native D50, i.e. the D50 characteristic to the oleosomes inside the source of origin before being extracted therefrom.

The sources of origin for the oleosomes used in the present invention may be any cells containing oleosomes or oleosomes-like organelles. This includes animal cells, plant cells, fungal cells, yeast cells, bacterial cells and algae cells. In preferred embodiments of the invention the oleosomes are obtained from a plant cell which includes cells from pollens, spores, seed and vegetative plant organs in which oleosomes or oleosomes-like organelles are present (Huang, 1992, Ann. Rev. Plant Physiol. 43: 177-200). Preferably, the sources of origin of the oleosomes used in accordance with the invention are members of the Brassicaceae, Amaranthaceae, Asparagaceae, Echium, Glycine, Astaraceae, Fabaceae, Malvaceae, Faboidae, Aracaceae, Euphorbiceae, Sinapsis, Lamiaceae, Cyperaceae, Anacardiaceae, Rosaceae, Betulaceae, Juglandaceae, Oleaceae, Lauraceae, Sapotaceae and/or Poaceae families. More preferably, the oleosomes are obtained from a plant seed and most preferably from the group of plant species comprising: rapeseed (*Brassica* spp.), soybean (*Glycine max*), sunflower (*Helianthus annuits*), oil palm (*Elaeis guineeis*), cottonseed (*Gossypium* spp.), groundnut (*Arachis hypogaea*), coconut (*Cocus nucifera*), castor (*Ricinus communis*), safflower (*Carthamus tinctorius*), mustard (*Brassica* spp. and *Sinapis alba*), coriander (*Coriandrum sativum*), squash (*Cucurbita maxima*), linseed/flax (*Linum usitatissimum*), Brazil nut (*Bertholletia excelsa*), hazelnut (*Corylus avellana*), walnut (*Juglands major*), jojoba (*Simmondsia chinensis*), thale cress (*Arabidopsis thaliana*), wheat and wheat germ (*Triticum* spp.), maize and maize germ (*Zea mays*), amaranth (family of *Amaranthus*), sesame (*Sesamum indicum*), oat (*Avena*

*sativa*), camelina (*Camelina sativa*), lupin (*Lupinus*), peanut (*Arachis hypogaea*), quinoa (*Chenopodium quinoa*), chia (*Salvia hispanica*), yucca, almond (*Prunus dulcis*), cashew (*Anacardium occidentale*), olive (*Olea*), avocado (*Persea americana*), shea (*Butyrospermum parkii*), cocoa bean (*Theobroma cacao*), argan (*Argania spinosa*) and rice. Oleosomes other than those derived from plants may also be used in the present invention. A system functionally equivalent to plant oleosomes and oleosins has been described in bacteria (Pieper-Fürst et al., 1994, J. Bacteriol.176: 4328), yeast (Leber, R. et al., 1994, Yeast 10: 1421-1428), algae (Rossler, P. G., 1988, J. Physiol. (London), 24: 394-400) and fungi (Ting, J. T. et al., 1997, J. Biol Chem.272: 3699-3706). Oleosomes from these organisms, as well as those that may be discovered in other living cells by a person skilled in the art, may also be employed according to the subject invention.

Methods of producing oleosomes are well known in the art. Typically, plants are grown and allowed to set seed using agricultural cultivation practices well known to a person skilled in the art. After harvesting the seed and if desired removal of material such as stones or seed hulls (de-hulling), by for example sieving or rinsing, and optionally drying of the seed, the seeds are subsequently processed by mechanical pressing, grinding or crushing. A liquid phase, e.g. water, may also be added prior to grinding of the seeds, which is known as wet milling and has been reported for seeds from a variety of plant species including: mustard (Aguilar et al 1990, journal of Texture studies 22:59-84), soybean (U.S. Pat. No. 3,971,856; Carter et al., 1974, J. Am. Oil Chem. Soc. 51:137141), peanut (U.S. Pat. Nos. 4,025,658; 4,362, 759), cottonseed (Lawhon et al., 1977, J. Am. Oil, Chem. Soc. 63:533-534) and coconut (Kumar et al., 1995, INFORM 6 (11):12171240). Following grinding, a homogenate is obtained which is filtrated. The filtrate may be subsequently centrifuged to extract the oleosomes with their associated proteins therefrom. The oleosomes may be subsequently washed, however, it is desirable that aggregates of oil bodies are dissociated as thoroughly as possible in order to ensure efficient removal of contaminants in the subsequent washing steps. The oleosomes may be washed by e.g. re-suspending them in a floatation solution of lower density (e.g. water, aqueous buffer) and centrifuged, again, separating the oleosomes and aqueous phases. This washing procedure is typically repeated between one and three times after which the oleosomes are deemed to be sufficiently free of contaminating soluble proteins as determined by gel electrophoresis (e.g. SDS-PAGE). Protocols for isolating oleosomes from oil seeds are available in WO2012/110797; WO 98/53698; EP 1 007 554; Murphy, D. J. and Cummins I., 1989, Phytochemistry, 28: 2063-2069; and in: Jacks, T. J. et al., 1990, JAOCS, 67: 353-361.

The oleosomes may be used as extracted or they may be further processed to adjust their natural D50 to the desired range. It should be also noted that various species of seed from the same genus or family exist, e.g. sunflower seeds or rapeseeds, which may contain oleosomes having different D50. In such cases, the skilled person may choose seeds which deliver oleosomes having the D50 within the desired range.

In a preferred embodiment of the inventive composition, the first oleosomes are extracted from sources of origin chosen from the group consisting of soybean, rapeseed, corn, mustard, cottonseed, wheat, wheat germ, maize, maize germ and camelina; and the second oleosomes are extracted from sources of origin chosen from the group consisting of linseed, amaranth, peanut, sesame, cashew, almond, sunflower, oil palm, coconut, safflower, Brazil nut, hazelnut, walnut, olive, avocado, shea, argan, jojoba, and cocoa; provided that when combining the first and second oleosomes the respective D50s thereof fulfill the invention's requirements, i.e. $D50(1)$ is different than $D50(2)$, preferably $D50(1) \leq D50(2)$.

In another preferred embodiment of the inventive composition, the first oleosomes are extracted from soy seeds (also known as soybean) or corn seeds and the second oleosomes are extracted from rapeseeds or sunflower seeds. In another embodiment, the first oleosomes are extracted from soy seeds or corn seeds and the second oleosomes are extracted from rapeseeds. The inventors observed that such compositions may have an increased usability and optimal aggregation behavior.

In another preferred embodiment of the inventive composition, the first oleosomes are extracted from soy and the second oleosomes are extracted from amaranth. The inventors observed that such composition is highly beneficial in personal care products such as cosmetics and in pharmaceutical products such as vaccines.

In yet another preferred embodiment of the inventive composition, the first oleosomes are extracted from seeds chosen from the group consisting of rapeseed, soy, mustard and corn and the second oleosomes are extracted from peanut seeds. The inventors observed that such composition may help in taste optimization and against unwanted oxidation.

In yet another preferred embodiment of the inventive composition, the first oleosomes are extracted from seeds chosen from the group consisting of rapeseed, soy, mustard and corn and the second oleosomes are extracted from sesame seeds. The inventors observed that such composition may help in flavor masking.

In yet another preferred embodiment of the inventive composition, the first oleosomes are extracted from corn seeds and the second oleosomes are extracted from seeds chosen from the group consisting of rapeseed, peanut, sesame, flax and sunflower.

In yet another preferred embodiment of the inventive composition, the first oleosomes are extracted from soy seeds and the second oleosomes are extracted from seeds chosen from the group consisting of rapeseed, peanut, sesame, flax and sunflower.

In yet another preferred embodiment of the inventive composition, the first oleosomes are extracted from soy bean and the second oleosomes are extracted from almond, peanut, sunflower, coconut or sesame. Further improved results are obtained when instead of the soybean oleosomes, corn, corn germ, cashew or mustard oleosomes are used.

In yet another preferred embodiment of the inventive composition, the second oleosomes are extracted from sunflower and the first oleosomes are extracted from soy, corn, corn germ, cashew, linseed or mustard oleosomes. Good results are also obtained when the first oleosomes are extracted from corn and the second oleosomes are extracted from rapeseed.

In yet another preferred embodiment, the inventive composition comprises also third oleosomes having a D50 (hereinafter $D50(3)$) which is different than $D50(1)$ and $D50(2)$. Preferably, $D50(3) < D50(2)$, while $D50(3)$ can be smaller or larger than $D50(1)$. The inventors observed that such a composition containing a third kind of oleosomes, different than the first and the second oleosomes, may enable a finer tuning or modulating of the composition's properties, e.g. rheological, sensorial, taste profile and the like.

Preferably, the D90 of the first oleosomes, hereinafter D90(1), is at least 400 nm, more preferably at least 500 nm, most preferably at least 600 nm. Preferably, D90(1) is at most 2500 nm, more preferably at most 2200 nm, most preferably at most 1900 nm. In a preferred embodiment, D90(1) is between 400 nm and 2200 nm, more preferably between 500 nm and 2000 nm, most preferably between 600 nm and 1800 nm.

In a preferred embodiment, the D90 of the first oleosomes, hereinafter D90(1), is at least 500 nm, more preferably at least 900 nm, most preferably at least 1400 nm. Preferably, D90(1) is at most 2500 nm, more preferably at most 2200 nm, most preferably at most 1900 nm. In a preferred embodiment, D90(1) is between 500 nm and 2200 nm, more preferably between 1200 nm and 2000 nm, most preferably between 1400 nm and 1800 nm.

Preferably, the D90 of the second oleosomes, hereinafter D90(2), is at least 1500 nm, more preferably at least 2000 nm, most preferably at least 2500 nm. Preferably, D90(2) is at most 25000 nm, more preferably at most 22000 nm, most preferably at most 19000 nm. In a preferred embodiment, D90(2) is between 1500 nm and 22000 nm, more preferably between 2000 nm and 20000 nm, most preferably between 2500 nm and 19000 nm.

In a preferred embodiment, the D90 of the second oleosomes, hereinafter D90(2), is at least 3000 nm, more preferably at least 3300 nm, most preferably at least 3500 nm. Preferably, D90(2) is at most 25000 nm, more preferably at most 22000 nm, most preferably at most 19000 nm. In a preferred embodiment, D90(2) is between 3000 nm and 22000 nm, more preferably between 3200 nm and 20000 nm, most preferably between 3400 nm and 19000 nm.

Preferably, the D10 of the first oleosomes, hereinafter D10(1), is at least 50 nm, more preferably at least 70 nm, most preferably at least 90 nm. Preferably, D10(1) is at most 570 nm, more preferably at most 450 nm, most preferably at most 330 nm. In a preferred embodiment, D10(1) is between 50 nm and 570 nm, more preferably between 70 nm and 450 nm, most preferably between 90 nm and 330 nm.

Preferably, the D10 of the second oleosomes, hereinafter D10(2), is at least 160 nm, more preferably at least 250 nm, most preferably at least 340 nm. Preferably, D10(2) is at most 3500 nm, more preferably at most 3000 nm, most preferably at most 2500 nm. In a preferred embodiment, D10(2) is between 160 nm and 3500 nm, more preferably between 250 nm and 3000 nm, most preferably between 340 nm and 2500 nm.

Preferably, the PD=(D90−D10)/D50 of the first oleosomes, hereinafter PD(1), is at least 0.50, more preferably at least 1.0, most preferably at least 1.5. Preferably, PD(1) is at most 3.0, more preferably at most 2.5, most preferably at most 2.0. In a preferred embodiment, PD(1) is between 0.5 and 3.0, more preferably between 1.0 and 2.5, most preferably between 1.5 and 2.0.

Preferably, the PD of the second oleosomes, hereinafter PD(2), is at least 0.5, more preferably at least 0.7, most preferably at least 1.0. Preferably, PD(2) is at most 5.0, more preferably at most 4.5, most preferably at most 4.0. In a preferred embodiment, PD(2) is between 0.5 and 5.0, more preferably between 0.7 and 4.5, most preferably between 1.0 and 4.0.

The present inventors surprisingly observed that by combining the oleosomes in accordance with the present invention, inventive compositions may be obtained having increased amounts of tocopherol and/or phytosterol per unit of volume of composition. Preferably, the first oleosomes are in a volume fraction $\Phi_1$ and the second oleosomes are in a volume fraction $\Phi_2$ wherein $\Phi_1:\Phi_2$ is from 10:90 to 90:10, more preferably between 20:80 and 80:20, even more preferably between 30:70 and 70:30, most preferably between 40:60 and 60:40.

The inventive composition may be obtained by mixing aqueous solutions of first and second oleosomes but also by mixing dry first and second oleosomes as well as combinations thereof. The drying of the oleosomes can be achieved by any method known in the art, e.g. vacuum drying, freeze drying and the like. Preferably, the oleosomes are dried using a freeze drying method. Most preferred method to obtain the inventive composition is by mixing an aqueous solution of the first oleosomes with an aqueous solution of the second oleosomes. Preferably, the oleosomes used in the present invention are washed to remove unwanted components to the extent the oleosomes containing at least 90 wt % triglycerides, between 0.5 wt % and 2.5 wt % phospholipids and between 2 wt % and 6 wt % intrinsic proteins are obtained.

The inventive composition may be in a liquid form, preferably in an aqueous solution form; but it may also be in a dry form, i.e. having a moisture content of at most 40 wt %, more preferably at most 30 wt %, most preferably at most 20 wt %.

The inventors observed that the inventive composition has an optimum shear thinning behavior. For instance, it was observed that the viscosity variation with the shear rate of the inventive composition at shear rates above 30 sec$^{-1}$ and in particular above 50 sec$^{-1}$ is improved over that of compositions containing a single kind of oleosomes. Without being bound to any theory, the inventors believe that such surprising improvement in viscosity is due to a synergistic interaction between the at least two kinds of oleosomes present in the inventive composition. Such peculiar shear thinning behavior, i.e. optimum viscosity variation at small shear rates (e.g. below 10 sec$^{-1}$) and at larger shear rates (e.g. between 30 sec$^{-1}$ and 100 sec$^{-1}$) is highly desirable for a multitude of food products, e.g. spreads, but also for a multitude of personal care products, e.g. lotions, creams and the like.

The inventors also surprisingly observed that the inventive composition has a surprisingly stable G', e.g. stability in time but also versus strain and frequency in particular in the linear visco-elastic range. Such stability is highly beneficial for instance in food products since the mouthfeel and other organoleptic properties of said products is typically related thereto. Also for personal care products, such stability is beneficial in particular for lotions and crèmes.

The inventors also surprisingly observed that the inventive composition can be easily adjusted to yield an optimum yield stress, which is beneficial when utilized in various food, pharmacological and personal care applications, such as ketchup, mayonnaise but also tooth paste and other lotions and ointments.

An important benefit of the inventive composition is that all of the above rheological parameters can be tuned as desired by choosing the appropriate combination of oleosomes.

Preferably, at least one additional ingredient is added to the inventive composition. The additional ingredient may be added as a solution, suspension, a gel or solid and quantities of the additional ingredient will depend on the formulation. The additional ingredient may upon formulation become associated with the oleosomes, remain suspended in solution, or form a suspension in which the oleosomes are dispersed. The ingredient may also penetrate the phospholipid monolayer surrounding the oleosomes or the triacylglyceride matrix. Ingredients which may penetrate the oleosomes include oils, waxes, colorants, phytosterols, phospholipids, oil soluble vitamins (e.g. Vitamin E) and oil soluble flavors.

In a preferred embodiment, the additional ingredient is a liquid phase. In a further preferred embodiment the liquid phase is water. Water may be added either directly or through moisture associated with another ingredient. The final amount of water is not critical, as long as upon mixing of the ingredients, a stable emulsion is formed. As specified above, the inventive composition may contain water in various amounts, e.g. from at least 1% of water and up to 99% water. Usually mixing will be required to provide an adequate emulsion starting from the inventive composition and it may be necessary to apply heat or pressure.

In another preferred embodiment the additional ingredient is an oil or a wax. Oils or waxes may partition to the triacyl glyceride matrix of the oleosomes and in this manner lipid soluble ingredients, such as lipid soluble vitamins may be delivered to the oleosomes matrix. Where oils or waxes comprise the added ingredient, the oleosomes may remain suspended in the lipophilic phase or double emulsions may be formed.

The inventive composition may be formulated into a water-in-oil (W/O) or an oil-in-water (O/W) emulsion using techniques known in the art. Double and multiple emulsions of these kinds can also be manufactured using the inventive composition. The invention relates therefore to an emulsion containing the inventive composition and preferably an additional ingredient, examples of which are listed above.

The inventive emulsion may be in solid or in liquid form or of any other desired viscosity. Said emulsion may be thickened using gelling agents such as cellulose and derivatives, citrus fibers, Carbopol and derivatives, carob, carregeenans and derivatives, xanthane gum, sclerane gum, long chain alkanolamides, starch and bentone and derivatives, typically present in concentrations less than 10% by weight, preferably less than 5% by weight relative to the weight of the emulsion. The most preferred gelling agent is citrus fibers.

The inventive composition or the inventive emulsion may further comprise surfactants to wet, foam, penetrate, emulsify, solubilize and or disperse a selected material. For example anionic surfactants such as sodium lauryl sulfate (SLS or SDS), sodium coconut monoglyceride sulphonate, cationic surfactants, such as lauryl trimethyl ammonium chloride, cetyl pyridinium chloride and trimethylammonium bromide, nonionic surfactants including pluronics, and polyethylene oxide condensates of alkyl phenols, and zwitterionic surfactants such as derivatives of aliphatic quaternary ammonium, phosmomium and sulphonium compounds may all be added as required.

Chelating agents, capable of binding metal ions, such as tartaric acid, EDTA, citric acid, alkali metal citrates, pyrophosphate salts or anionic polymeric polycarboxylates may be also included in the inventive composition or in the inventive emulsion as desired.

Generally, the inventive composition or the inventive emulsion will be treated such that contamination by bacteria, fungi, mycoplasmas, viruses and the like or undesired chemical reactions, such as oxidative reactions are prevented. Preferably, the inventive composition or the inventive emulsion is pasteurized. In other embodiments the treatment is accomplished by the addition of preservatives, for example sodium metabisulfite or other chemical additives or by irradiation, for example by ionizing radiation such as cobalt-60 or cesium-137 irradiation or by ultraviolet irradiation.

In addition, active agents may be added to the inventive composition or to the inventive emulsion. For example cosmetic compositions, e.g. a skin cream, may be formulated as stable suspensions using for instance the inventive emulsion and vitamins and moisturizing agents may be included therein. One particularly advantageous way in which an active ingredient may be included is through construction of oleosin gene fusions as detailed in WO 96/21029.

The inventive composition and/or the inventive emulsion are useful in industrial and domestic compositions. It is noted that the compositions and/or emulsions may be applied in products which vary widely in physical properties and use. Thus specific embodiments include applications such as food and feed products, pharmaceutical products, personal care products and industrial products.

Examples of food products comprising the inventive composition or the inventive emulsion include: drinks and luxury drinks, such as coffee, black tea, powdered green tea, cocoa, adzuki-bean soup, juice, soya-bean juice, etc.; milk component-containing drinks, such as raw milk, processed milk, lactic acid beverages, etc.; a variety of drinks including nutrition-enriched drinks, such as calcium-fortified drinks and the like and dietary fiber-containing drinks, etc.; dairy products, such as butter, cheese, vegan cheese, yogurt, coffee whitener, whipping cream, custard cream, custard pudding, etc.; iced products such as ice cream, soft cream, lacto-ice, ice milk, sherbet, frozen yogurt, etc.; processed fat food products, such as mayonnaise, margarine, spread, shortening, etc.; soups; stews; seasonings such as sauce, TARE, (seasoning sauce), dressings, etc.; a variety of paste condiments represented by kneaded mustard; a variety of fillings typified by jam and flour paste; a variety or gel or paste-like food products including red bean-jam, jelly, and foods for swallowing impaired people; food products containing cereals as the main component, such as bread, noodles, pasta, pizza pie, corn flake, etc.; Japanese, US and European cakes, such as candy, cookie, biscuit, hot cake, chocolate, rice cake, etc.; kneaded marine products represented by a boiled fish cake, a fish cake, etc.; live-stock products represented by ham, sausage, hamburger steak, etc.; daily dishes such as cream croquette, paste for Chinese foods, gratin, dumpling, etc.; foods of delicate flavor, such as salted fish guts, a vegetable pickled in sake lee, etc.; liquid diets such as tube feeding liquid food, etc.; supplements; and pet foods. These food products are all encompassed within the present invention, regardless of any difference in their forms and processing operation at the time of preparation, as seen in retort foods, frozen foods, microwave foods, etc. Preferably, the food product has a pH of between 4 and 6.

In a particular embodiment, the invention relates to a product chosen from the group consisting of food products, feed products, pharmaceutical products, personal care products and industrial products, said product comprising the inventive composition or inventive emulsion and having a TOCT content of at least 60 wt %, preferably at least 63 wt %, more preferably at least 66 wt %, most preferably at least 69 wt % of the total weight of the product. Preferably, the product is a spreadable product, more preferably a spreadable food product.

The inventive composition or inventive emulsion may be employed to prepare ice creams, milkshakes or other frozen food-grade materials with improved freezing properties by inhibiting or preventing ice crystal formation.

The inventive composition or inventive emulsion may also be used to formulate a desirable suspension which may be for oral consumption, or for topical skin application.

The inventive emulsion may also be used in sprays and aerosols. Volatiles, such as alcohol and fragrances may be included in these sprays. Emulsions of this type may also be sprayed onto the surface of dried food preparations and frying goods, e.g. potato chips, nuggets and dried soup. The emulsion might include a flavorant and add preservative value or assist in maintaining the appropriate moisture levels of the food.

The inventive composition or inventive emulsion may also be employed to prepare an animal feed such as dry or moisture-containing feed. Preferred animal feeds are fish, chicken and swine feed which contain the inventive composition or inventive emulsion. In a particularly advantageous embodiment, the emulsion may be formulated to have film forming properties may also be formulated. Such an emulsion when applied to a surface and dried forms a film thereon. An example of an emulsion where a film containing the inventive composition is applied is in fish or chicken food, where oleosomes may be applied to the fish or chicken food to enhance the dietary value.

A film forming emulsion is also particularly useful in embodiments of the present invention where controlled release of an active ingredient is desirable such as in delivery of pharmaceuticals or volatiles such as fragrances. The release time of the active agent from a film of emulsion, which occurs during drying, depends, among other factors, on the thickness of the film. When a thicker coating is applied a longer drying time will result in a slower release of the active agent. In variant contemplated formulations, release of the agent occurs only when the film is dry. Other factors, such as the composition of the emulsion and the type and concentration of the active ingredient also determine the characteristics of release. For example, cosolvents, such as ethanol, may be included in the formulation and influence the release time. Release of an active ingredient is also desirable in food applications, where a flavorant entrapped in an emulsion is released during consumption. The release of the flavorant, depending on the exact formulation of the emulsion, may elicit a sudden intense sensation or a more subtle blend of flavors and essences.

Preferred food and feed uses include non-dairy substitutes, such as non-dairy cheese or yoghurt, margarines, mayonnaises, vinaigrettes, icings, ice creams, salad dressings, synthetic mustards, candy, chewing gum, pudding, baking products, condiments, juice clouding agents, baby formula, flavor carriers, texturing agents (shortening), pet food, fish food and livestock feed.

In another embodiment, the inventive composition or the inventive emulsion is a buffered emulsion having an isoelectric point and a zeta potential, wherein the absolute difference between the zeta potential and the isoelectric point is at least 10 mV. By isoelectric point of said emulsion is herein understood the point at which the zeta potential of the product is zero millivolts (mV). The present inventors observed that the zeta potential of said emulsion can be used to influence the aggregation of the oleosomes contained thereby. For instance, by carefully adjusting said zeta potential, the inventors were able to achieve fine dispersions of the oleosomes in products containing thereof with an unprecedented oleosome distribution.

Personal care products containing the inventive composition or the inventive emulsion include soaps, cosmetics, skin creams, facial creams, tooth paste, lipstick, perfumes, make-up, foundation, blusher, mascara, eyeshadow, sunscreen lotions, hair conditioner, and hair coloring.

Pharmaceutical products containing the inventive composition or the inventive emulsion may be formulated to include therapeutic agents, diagnostic agents and delivery agents. As a therapeutic or diagnostic agent, the product will additionally contain an active ingredient. The active ingredient can be anything that one wishes to deliver to a host. In one embodiment, the active ingredient may be a protein or peptide that has therapeutic or diagnostic value. Such peptides include antigens (for vaccine formulations), antibodies, cytokines, blood clotting factors and growth hormones. A preferred pharmaceutical product is a parenteral emulsion containing the inventive composition or the inventive emulsion and a drug.

In a particularly preferred embodiment, the invention relates to an O/W parenteral emulsion formulation containing the inventive composition or the inventive emulsion, for the parenteral administration of drugs. Drugs may be incorporated into said emulsion either by emulsification of the drug dissolved in the oil phase, or by extemporaneous addition of a concentrated solution in a (co)solvent. Said parenteral emulsion may be used to deliver drugs which have low water solubility, lack stability to hydrolysis, are irritant or have substantial affinity for plastic infusion sets.

Industrial uses of the inventive composition or the inventive emulsion include paints, coatings, lubricants, films, gels, drilling fluids, paper sizing, latex, building and road construction material, inks, dyes, waxes, polishes and agrochemical formulations.

In preferred embodiments, the subject invention is directed to products containing the inventive composition or the inventive emulsion which may be ingested by animals and humans. Since, these products may be ingested they must be of food-grade quality.

The stability of the inventive composition or of the inventive emulsion may be exploited during the preparation of various products such as a spread or a mayonnaise-like food product, which besides the inventive composition or inventive emulsion may comprise a vegetable oil, mustard, vinegar and/or egg yolk, if desired. Pourable emulsions, such as salad dressings may be prepared by increasing the relative amount of vinegar and/or by the addition of water. An example of an application where heat may be applied without apparent deleterious effects, is in the preparation of a savory sauce such as a béchamel sauce or in sweet sauces such as chocolate sauces.

The inventive composition or inventive emulsion may thus also be employed as a frying substitute. To prepare a béchamel sauce, to 1 part of the heated inventive composition or emulsion, 1 part (w/w) of flour is added and stirred until a thick suspension is formed. At moderate heat milk is gradually added until a sauce with a desired viscosity is obtained.

The inventive composition or inventive emulsion may also be used as a butter substitute. In this application, small amounts of water are thereto, for example, less than 10% until a desired viscosity is obtained. Natural butter flavors and thickeners may be added as desired. The butter substitute may be used on sweet corn, bread, in cake mixes or bread making. Salt, which contributes flavor and acts as a preservative may be added typically to a level of about 2.5% (wt/vol.). Color agents, for example, extracts of annatto seed or carotene may be added to deepen the color as desired. An advantage of this application is that the oleosome based butter does not comprise hydrogenated fatty acids, which are used in the formulations of margarines and the like to achieve a desirable consistency, but are also with associated with cardiovascular diseases.

Shortenings containing the inventive composition or the inventive emulsion may be prepared to various degrees of stiffness, from a foam to a pourable shortening. In this application, air is beaten into inventive composition or inventive emulsion which can be considered to be dispersed into the continuous phase, air. Shortenings may be applied to mixes where creaming and fluffing are desired. These mixes include icings, synthetic creams, ice creams and cake batter.

An imitation fruit juice containing the inventive composition or the inventive emulsion may be prepared containing also artificial or natural flavors and nutrients. Such imitation juices may be manufactured to have a reach appearance by adding a small amount, for example 0.1 to 1% (v/v) of the inventive composition or inventive emulsion. The present inventive composition or inventive emulsion may also be used as a clouding agent.

In another application involving juices, the inventive composition or inventive emulsion may be added to juices with settling-able solids, such as tomato juice. Adding a small amount of the inventive composition or inventive emulsion, for example 0.1 to 1% (v/v), may decrease the rate of settling of the solids in the juice and assist in maintaining the rich appearance.

Topical applications of the inventive composition or inventive emulsion are also envisaged. In this embodiment the inventive composition or inventive emulsion is formulated as a dermatologically acceptable emulsion, which may for example be employed to moisturize facial and/or body skin, including nails and lips or may have properties to combat ageing of the skin, acne, pigmentation, hair loss, or promote hair removal or facilitate wound healing and/or restructuring of the skin tissue. The inventive composition or inventive emulsion represents preferably 1-99% by weight of the final composition.

Cosmetic compositions containing the inventive composition or the inventive emulsion may comprise additional hydrocarbon compounds such as plant, animal, mineral or synthetic oils or waxes or mixes thereof. They comprise paraffin, petrolatum, perhydrosqualene, arara oil, almond oil, calphyllum oil, avocado oil, sesame oil, castor oil, jojoba oil, olive oil, or cereal germ oil. Esters may be included such as esters of lanolic acid, oleic acid, lauric acid, stearic acid, myristic acid. It is also possible to include alcohols for example, oleoyl alcohol, linoleyl alcohol or linolenyl alcohol, isostearyl alcohol or octyl dodecanol, alcohol or polyalcohol. Further hydrocarbons which may be included are octanoates, decanoates, ricinoleates, caprylic/capric triglycerides or C10 to C22 fatty acid triglycerides. Addition of these agents may result in the formation of double emulsions.

Hydrogenated oils, which are solid at 25° C., such as hydrogenated castor oil, palm oil or coconut oil, or hydrogenated tallow; mono-di-tri- or sucroglycerides; lanolins; and fatty acids which are solid at 25° C. may also be included in the cosmetic formulations of the present invention. Among the waxes which may be included are animal waxes such as beeswax; plant waxes such as carnauba wax, candelilla wax, ouricurry wax, Japan wax or waxes from cork fibers or sugar cane; mineral waxes, for example paraffin wax, lignite wax, microcrystalline waxes or ozokerites and synthetic waxes.

Pigments may be included and may be white or colored, inorganic or organic and/or pearlescent. These pigments comprise titanium dioxide, zinc oxide, zirconium dioxide, black, yellow, red and brown iron oxides, cerium dioxide, chromium oxide, ferric blue, carbon black, barium, strontium, calcium and aluminum lakes and mica coated with titanium oxide or with bismuth oxide.

Active ingredients commonly employed in skin creams, such as vitamins, for example as vitamin A or C and alpha hydroxy acids, such as citric, glycolic, lactic and tartaric, into cosmetic and/or dermatological compositions may be included. For example, U.S. Pat. No. 5,602,183 teaches that vitamin C or ascorbic acid promotes growth of connective tissue particularly in the skin strengthens the skin against external aggressions such as from smoke and UV radiation.

Moisturizing agents which may be included in skin creams and cosmetics are for example mineral oil and urea. Antioxidants such as the naturally occurring tocopherols and polyphenols, or butylated hydroxytoluene and hydroxyanisole may also be also added. Sunscreens such as octyl methoxycinnamate (Parsol MCX), 3-benzophenone (Uvinul M40) and butylmethoxydibenzoylmethane (Parsol 1789) may be employed to prepare a sun tanning lotion. Pharmaceutically active ingredients which may be used to formulate cosmetic compositions include for example antibiotics, fungicides and anti-inflammatory agents.

The final cosmetic product may be in the form of a free, poured or compacted powder (foundation, blusher or eyeshade), a relatively greasy product such as lipstick, mascara, or an oil or lotion for the body or face.

The inventive composition or inventive emulsion may also be used to serve as an orally acceptable carrier in toothpaste which may further comprise silica, surfactants, chelating agents, a fluoride, thickeners, sweeteners, flavorants, for example as oil of peppermint, enzymes and biocides.

An example of an industrial product which may be formulated is paint wherein the main resin, such as those based on silicone type compounds, acrylic compounds, polyester, akyd, fluorine, epoxy, polyurethane may be partly or entirely replaced by the inventive composition or inventive emulsion. Further additives such as pigments, dyes, glass flakes, and aluminum flakes, pigment dispersants, thickeners, levelling agents, hardening catalysts, hardening agents such as dioisocyanates, hardening catalysts, gelling inhibitors, ultraviolet absorbing agents, free radical quenching agents-etc. may be formulated in paint compositions as required.

The inventive composition or inventive emulsion may also be to formulate lubricants. For example, the inventive composition or inventive emulsion may be used to partially or entirely replace the lubricating oils such as animal oils, vegetable oils, petroleum lubricating oils, synthetic lubricating oils, or the lubricating grease such as lithium grease, urea grease and calcium grease. Other compositions employed in a lubricant formulation comprise antioxidants, detergent dispersants, oiliness agents, friction modifiers, viscosity index improvers, pour point depressants, solid lubricant material, rust inhibitors and antifoamers.

Waxes may also be prepared using the inventive composition or inventive emulsion. These comprise rinse-wax types, such as those providing a stable hydrophobic film-finish onto automobiles and other protective coatings. Other compositions used in the preparation of a wax comprise surfactants, mineral oils, such as mixed paraffinic and aromatic/naphtenic oils, perfumes, biocides, coloring agents which may be added in compatible amounts as desired.

Where industrial products, such as paints or lubricants are formulated, purity of the oleosomes phase may be less critical and it may not be necessary to subject the oleosomes to washing.

Methods of Measurement

Rheology Method 1 (with an Anton Paar rheometer): The rheological properties (e.g. viscosity, G', yield stress, etc.) of certain samples and products containing samples (e.g. spreads) were measured with a stress-controlled rheometer (MCR 301, Anton Paar, Graz, Austria) at 20° C. Cross hatched parallel plates with a diameter of 50 mm (PP50/P2) were used. After sample loading (trimming height at 1025 μm), the sample was subjected to an oscillatory time sweep at 1 mm gap. A constant strain amplitude of 0.01% and a frequency of 1 Hz were applied to the sample for 300 s (20 data points were collected) Immediately thereafter, the viscosity curve (viscosity versus shear rate) was measured by increasing shear rate linearly from 0.001 to 100 $s^{-1}$. 7 measuring points per decade of the shear rate were obtained and each shear rate was applied to the sample for 20 s.

Rheology Method 2 (with a TA Instruments rheometer):

Sample Preparation: Samples of oleosomes and mixtures thereof were adjusted to pH 5 and a dry substance (DS) of 63%. The pH was adjusted by creating a pH 5 buffer, directly in the final oleosomes obtained after the washing/extraction steps, and centrifugation at 4° C. for certain time, the smaller the oleosomes, the longer the time, e.g. 30 minutes for sunflower (SF) and rapeseed (RS) and 60 minutes for soybean (SB); at a varying speeds—the smaller the oleosomes, the higher the speed (rpm), e.g. 4000, 6000 and 10000 rpm for SF, RS and SB respectively. For almond (AM) oleosomes, the samples were first centrifuged (30 minutes, 10° C., 4000 rpm) and then the dry substance was adjusted to 63% with pH 5 buffer (previously mentioned). After this, the dry substance was adjusted to 63% using buffer (10 mM Acetic acid, pH 5; I=85.6 mM). For almond oleosomes (known as having a large size), the samples were first centrifuged (30 minutes, 10° C., 4000 rpm) and then the dry substance was adjusted to 63% with pH 5 buffer (previously mentioned). Blends of oleosomes were made by diluting to a dry solid content of 30%, mixing in chosen ratios, centrifugation, e.g. at 4000 rpm 4° C. for 10 min (AM/SB) or 30 min (SF/RS), and then readjusting the dry substance to 63%.

The rheological properties (e.g. viscosity, G', yield stress, etc.) was performed at pH 5.0 (DS 63%) on the samples and products containing individual oleosomes and bends thereof. Samples (e.g. spreads) were measured using a 20-mm serrated parallel plate with a gap of 1000 μm (Discovery HR-2 Rheometer, TA). Three types of sweeps were applied in order: a frequency sweep, followed by two different flow sweeps. In the first sweep the angular frequency was decreased from 10 to 0.1 rad/s, at a strain of 0.1%. In the second sweep the shear stress was increased from 0.1 Pa to 1000 Pa until a shear rate of 10 $sec^{-1}$ was reached. Immediately after reaching said shear rate, a third sweep was started where the shear rate was decreased from 100 to 0.1 $s^{-1}$. All measurements were performed at 10° C., and before the first and after the last sweep a time sweep was done with a fixed strain of 0.1% at 1 Hz for 300 seconds.

D50 of oleosomes is the diameter in microns that splits the oleosome distribution with half above and half below this diameter. For the purpose of the invention, the oleosomes were considered to be spherical and in case of non-spherical oleosomes, the diameter was considered as being the largest dimension that can be measured between two opposite points on the surface thereof. D50 was determined using a Mastersizer 2000 (or 3000) from Malvern wherein the size distribution is correlated with diffraction results by the mathematical approximation theory of Mie. The sizes are expressed in diameters of spheres that correspond to oleosomes of the same volume. The D50 of the oleosomes was measured right after isolation of the oleosomes. The oleosomes were measured in diluted form of approximately 0.2% oleosomes in buffer solution (10 mM sodium phosphate, pH 7.4) to avoid pH fluctuations while adding 1% sodium dodecyl sulfate to the buffer (surfactant generally used to measure real particle sizes by preventing flocculation conditions). All samples were stored at 4° C. for at least 3 hours before measurement. Samples were allowed to warm to room temperature prior to measurement. D50 was also performed before and after rheological measurements were done, in order to determine whether the sample changed when certain stresses and shearing forces were applied. The diluted oleosomes were added drop wise to the Mastersizer until the required obscuration was in range. The chosen refractive indexes for the particle and dispersant were 1.47 and 1.33 respectively and the chosen absorption index for the particle was 0.001. Every sample was measured 3 times and averages were calculated (Ref: Guide, O., Malvern Mastersizer 3000. Malvern Instruments Ltd).

The span calculation (PD) is the most common format to express distribution widths. Hence, D50 (μm) value, which is the diameter below which 50% of the volume of particles lies, and span (no unit), which is the wide of the distribution were analysed. The span is defined as: (D90−D10)/D50 where D10 and D90 are the diameters below which 10% and 90% of the volume of particles lie.

D90, D10 were measured in the same manner as D50.

Oxidative stability: was measured as specified in EP 1952695 A1 (see par. [0049] to [0054]).

A Phast system was used to perform SDS-PAGE (NuPAGE®-System from Life Technologies®) analysis. A gradient Phastgel (4-15%) with 6 lanes, of which 5 for samples and 1 for the marker (cfr. Materials) was used. The 5 samples were oleosomes extracted at various pHs between 8 and 12. First a Stock solution of 50 ml was made with 0.6 g Tris and 0.19 g EDTA adjusted to pH 8. Afterwards a working buffer was made with 5 ml Stock, 1 g SSDS, 0.077 g DTT and 5 mg Bromophenol Blue. Oleosome samples were diluted to 1% (w:v) in working buffer and 400 μl was loaded for each sample in the Phast system.

Oleosin: An SDS-PAGE analysis (NuPAGE®-System from Life Technologies®) was used to determine the oleosin content. NuPAGE® MES-Running Buffer and a 10% NuPAGE® Novex® Bis-Tris Mini Gel were applied according to the manufacturer's instructions but without heating, instead the oleosome samples were incubated 20 h with the NuPage®LDS Sample Buffer and the NuPage®LDS Reducing Agent. For visualization of the oleosin bands Coomassie® G-250 SimplyBlue® SafeStain (Invitrogen) was used. After staining for 1 h, the polyacrylamide gel was de-stained twice with ultrapure water for 1 h and subsequently for at least 20 h.

Moisture content: was determined by weighing a sample placed in a pre-dried vessel and subsequently heating the vessel containing the sample overnight in an oven at 105° C. The moisture content (in wt %) was calculated as (A1−A2)/A1×100 where A1 was the weight of the sample before drying in the oven and A2 was the weight of the resulted dried sample.

Isoelectric point and zeta potential: may be determined with a Horiba SZ-100 Autotitrator. Sample pH may be measured with the HORIBA 9621C temperature-compensated pH electrode after calibration using Horiba standard solution se 101-S.

The following non-limiting examples are illustrative of the preset invention.

Example 1

Rapeseed/Canola oleosomes were extracted as follows: 100 g rapeseeds where washed and soaked 12-20 h in de-ionized water at 4° C. The soaked seeds where crushed in cold de-ionized water with a total mass of 1 kg. The 10% rapeseed to water ratio was crushed in a Thermomix® TM5 at a speed of 10 700 rpm for 90 s and subsequently stirred at low speed at pH 9. The resulting slurry was filtered through two layers of Kimtechscience® precision wipes 21×11 cm (Kimberly Clark) or cheese cloth and the pH was adjusted to 11.0 with 1 N NaOH (Merck KGaA, Darmstadt, Germany) solution. The solution was filled into 50 ml centrifuge tubes (VWR), which were centrifuged in a Thermo Scientific™ Sorvall™ Legend™ XTR 4700 rpm at 4° C. for at least 5 h. The resulting cream layer (fat pat, oleosomes) were lifted with a small spoon and re-suspended at pH 11 and filled in new centrifuge tubes. This washing step (4700 rpm, 4° C., 3 h) was performed twice. The resulting oleosomes were collected and re-suspended at pH 10-11 and concentrations below 20% in de-ionized water and stored at 4° C.

Soybean oleosomes were extracted as follows: 100 g soybeans were washed and soaked 12-20 h in de-ionized water at 4° C. The soaked seeds where crushed in cold water de-ionized with a total mass of 1 kg. The 10% soybean to water ratio was crushed in a Thermomix® TM5 at a speed of 10 700 rpm for 90 s and subsequently stirred at low speed at pH 9. The resulting slurry was filtered through two layers of Kimtechscience® precision wipes 21×11 cm (Kimberly Clark) and the pH was adjusted to 11.0 with 1 N NaOH (Merck KGaA, Darmstadt, Germany) solution. The solution was filled into 50 ml centrifuge tubes (VWR), which were centrifuged in a Thermo Scientific™ Sorvall™ Legend™ XTR 10000 rpm at 4° C. for at least 5 h. The resulting cream layer (fat pat, oleosomes) were lifted with a small spoon and re-suspended at pH 11 and filled in new centrifuge tubes. This washing step (10000 rpm, 4° C., 3 h) was performed twice. The resulting oleosomes were collected and re-suspended at pH 10-11 and concentrations below 20% in de-ionized water and stored at 4° C.

The respective D50, D90 and D10 of the rapeseed oleosomes and of the soy oleosomes are presented in Table 1.

TABLE 1

|  | D50 (nm) | D90 (nm) | D10 (nm) |
|---|---|---|---|
| rapeseed | 600 | 2600 | 340 |
| soybean | 370 | 870 | 180 |

Examples 2-7

A number of compositions containing combinations of oleosomes fulfilling the invention's requirements were made as presented in Table 2. D50s are expressed in nm; wt % are relative to the total amount of the composition.

Isolation of oleosomes from the different sources (soybean (SB), sunflower (SF), canola rapeseed (RS) and almond (AM)) was accomplished by a modified aqueous-based flotation-centrifugation method following a methodology developed by Tzen, J. T. C., Peng, C. C., Cheng, D. J., Chen, E. C. F., & Chiu, J. M. H. (1997) *"A new method for seed oil body purification and examination of oil body integrity following germination"*.

Dried seeds were preconditioned by soaking in deionised (DI) water overnight at 4° C. (seed/DI water, 1/3, w/w). The soaking water was poured out, and the soaked seeds were washed once (seed/DI water, 1/2, w/w). DI water was added to obtain a 10% seed-to-water ratio and the mixture was subjected to intense homogenization with a Vorwerk Thermomix TM5 at the highest speed setting (10,700 rpm) for 90 s. The resulting slurries were respectively adjusted for sunflower, almond and rapeseed mixtures to pH 7.5, 8.0 and 9.0 with NaOH solution 1 N before filtering them through two layers of cheesecloth. Soybean slurry was directly filtered (no pH adjustment performed) through two layers of Kimtech science precision wipes 21×11 cm (Kimberly Clark) to obtain raw soy milk. After filtration, oleosomes were taken to pH 11.0. For almond milk, pH was kept at pH 8.

Every filtrate solution was filled into 50 ml centrifuge tubes (SuperClear), which were centrifuged at 4° C. in a Thermo Scientific Sorvall Legend XFR under different speed and time conditions depending on the oleosome type: soybean (5 h at 10,000 rpm), canola rapeseed (2 h at 6,000 rpm), sunflower (2 h at 4,000 rpm) and almond (30 min at 4,000 rpm).

After centrifugation, the floating oleosome-containing layer was collected and re-dispersed in new 50 ml centrifuge tubes with DI water (pH 11). This re-dispersion step was performed twice under the same centrifugation conditions as those described above according to the oleosome nature. The resulting oleosomes were finally collected, dispersed in DI water (pH 11) and stored at 4° C. until required. In the case of almond oleosomes, only one re-dispersion step was employed. The recovered almond oil bodies were gathered, dispersed in DI water (pH 8) and stored at 4° C.

TABLE 2

| | First oleosomes | | | | Second oleosomes | | | |
|---|---|---|---|---|---|---|---|---|
| | Source | D50 | D90 | D10 | Wt % | Source | D50 | D90 | D10 | Wt % |
| EX 2 | soybean | 290 | 600 | 120 | 40 | almond | 4500 | 7950 | 2380 | 60 |
| EX 3 | | | | | 10 | | | | | 90 |
| EX 4 | rapeseed | 660 | 1540 | 300 | 50 | sunflower | 5500 | 11450 | 1040 | 50 |
| EX 5 | | | | | 40 | | | | | 60 |
| EX 6 | | | | | 10 | | | | | 90 |
| EX 7 | rapeseed | 710 | 1630 | 320 | 60 | sunflower | 3770 | 7530 | 790 | 40 |

Example 8

A composition comprising three kinds of oleosomes was made having the characteristics as presented in Table 3. The oleosomes were obtained following the methods presented at Examples 2-7.

TABLE 3

| | D50 (nm) | D90 (nm) | D10 (nm) | Wt % |
|---|---|---|---|---|
| rapeseed | 660 | 1540 | 300 | 40 |
| soybean | 290 | 600 | 120 | 10 |
| sunflower | 5500 | 11450 | 1040 | 50 |

Example 9

Emulsions containing the four individual oleosomes (soybean, rapeseed, sunflower and almond) and the blends of Examples 2-8 were made by dispersing oleosomes in water in a manner similar to that presented above in the Sample Preparation section of RHEOLOGY METHOD 2 (RM2).

The rheological properties of the emulsions were investigated with RM2. For example, in FIG. 2(A-D) and FIG. 3(A-D), the viscosity (Pa*s) was measured and plotted as a function of stress (Pa) and as a function of shear rate (sec$^{-1}$), respectively, at a dry substance level of 63%.

Figure 2:
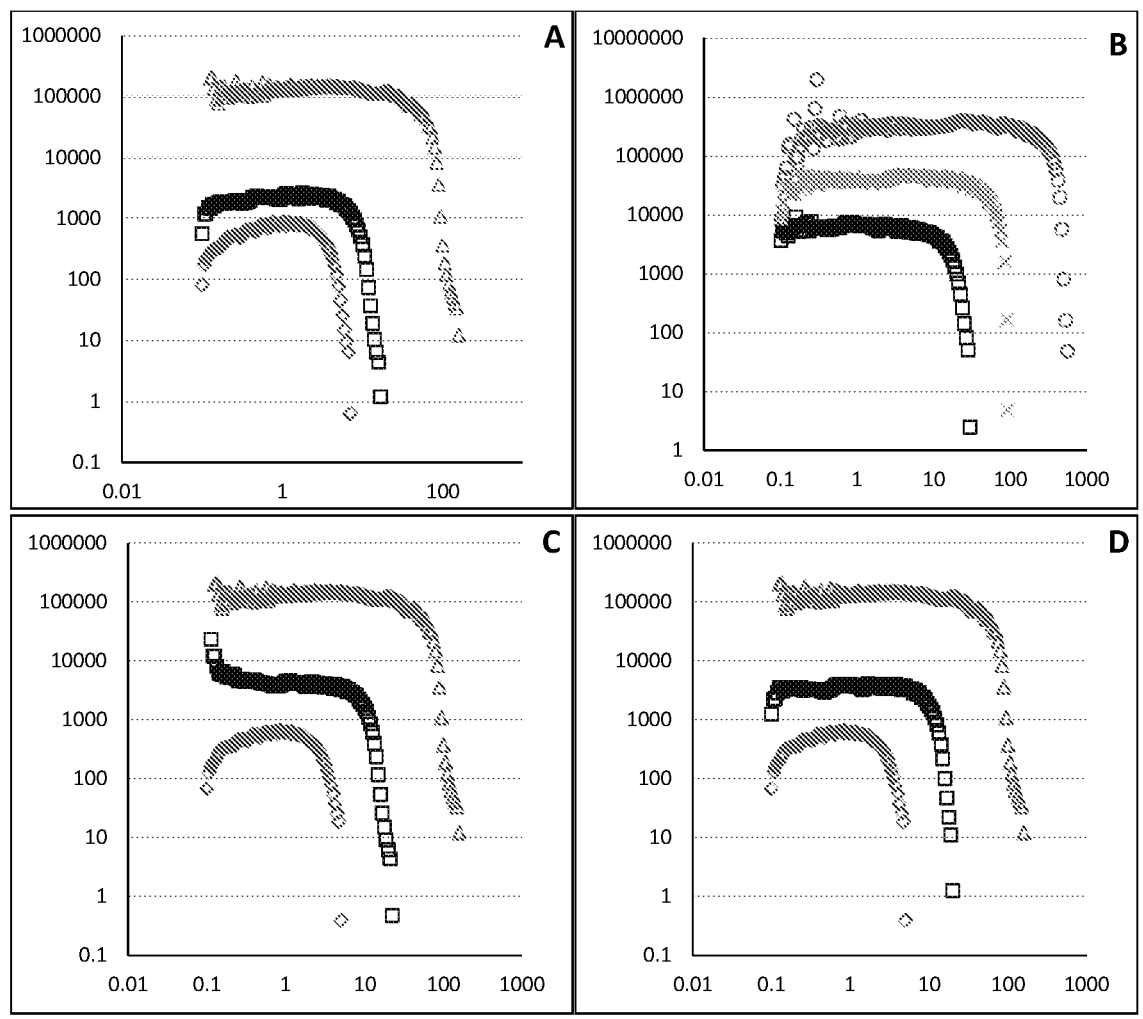
FIGS. 2 and 3 show the rheological behavior of various compositions of the invention.
Figure 3:
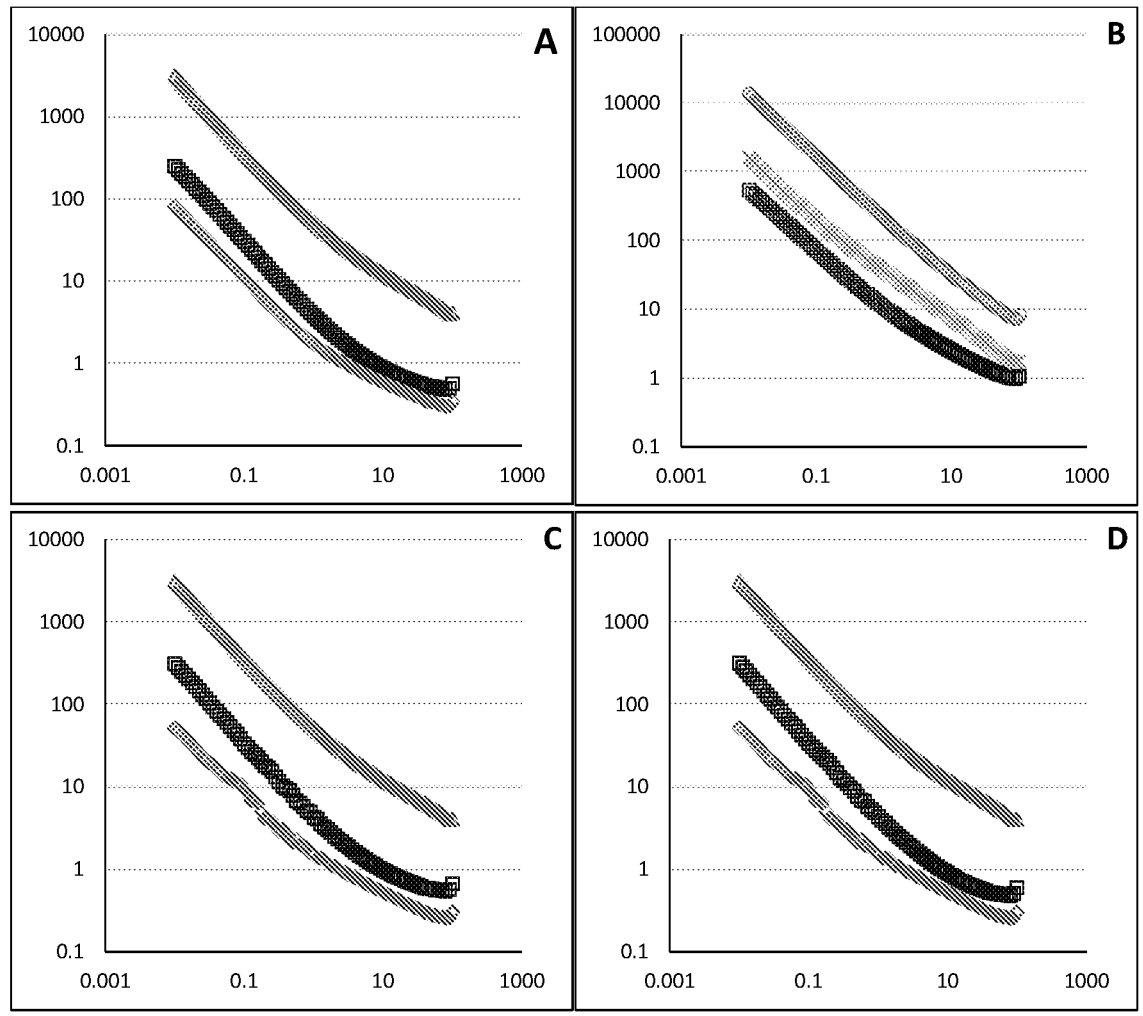

In said figures the following symbols were used: FIG. 2/3A—SF (◊), RS (Δ) and 60/40 SF/RS blend (□); FIG. 2/3B—AM (x), SB (o) and 60/40 AM/SB blend (□); FIG. 2/3C—SF (◊), RS (Δ) and 40/60 SF/RS blend (□); FIG. 2/3D—SF (◊), RS (Δ) and 50/50 SF/RS blend (□).

Storage (G) and Loss modulus (G') of each individual oleosome and of the mixtures thereof were also measured (not shown in Figures) and the inventors observed that the mixtures presented a gel-like behavior with the storage modulus of each sample being always higher than its loss modulus.

The inventors surprisingly observed that by combining different types of oleosomes at various ratios, one could modulate the rheological properties of the samples, e.g. viscosity, within wide ranges. From FIGS. 2 and 3, it becomes clear that by using the inventive compositions, one can modulate said rheological properties in a continuous fashion, rather than in discrete steps possible by using single kinds of oleosomes.

Most surprisingly, the inventors observed that the rheological properties of samples can be modulated to reach values even outside the boundaries set by the rheological properties of individual oleosomes. FIGS. 2B and 3B show a true synergistic behavior of the oleosomes contained by the inventive composition wherein the inventors by blending oleosomes, were able to go to lower viscosities than those of individual oleosomes. Such behavior to inventors' knowledge was never demonstrated hitherto in oleosomes based samples.

Example 10

A spread was made by adjusting a solution of extracted pure oleosomes to pH 5 containing the above mentioned oleosomes in a ratio rapeseed:soybean of 60:40. Denser packing of oleosomes was achieved by centrifugation at pH 5 in a Thermo Scientific™ Sorvall™ Legend™ XTR at 10000 rpm at 4° C. for at least 1 h or evaporation of water at pH 10-11. The rheological properties of said aqueous solution at pH 5 were investigated according to Rheology Method 1 and compared to pH 5 aqueous solutions containing rapeseed oleosomes and soy oleosomes only. The TOST content was about 70 wt %.

From FIG. 1A, one can immediately notice that the inventive composition (o) has at low shear rates a behavior superior to that of a composition containing rapeseed oleosomes only (◊) but similar to that of a composition containing soy oleosomes only (□). It is known that the smaller the D50 of oleosomes is, the more problematic their production is; however smaller oleosomes have advantageous properties.

Figure 1B:
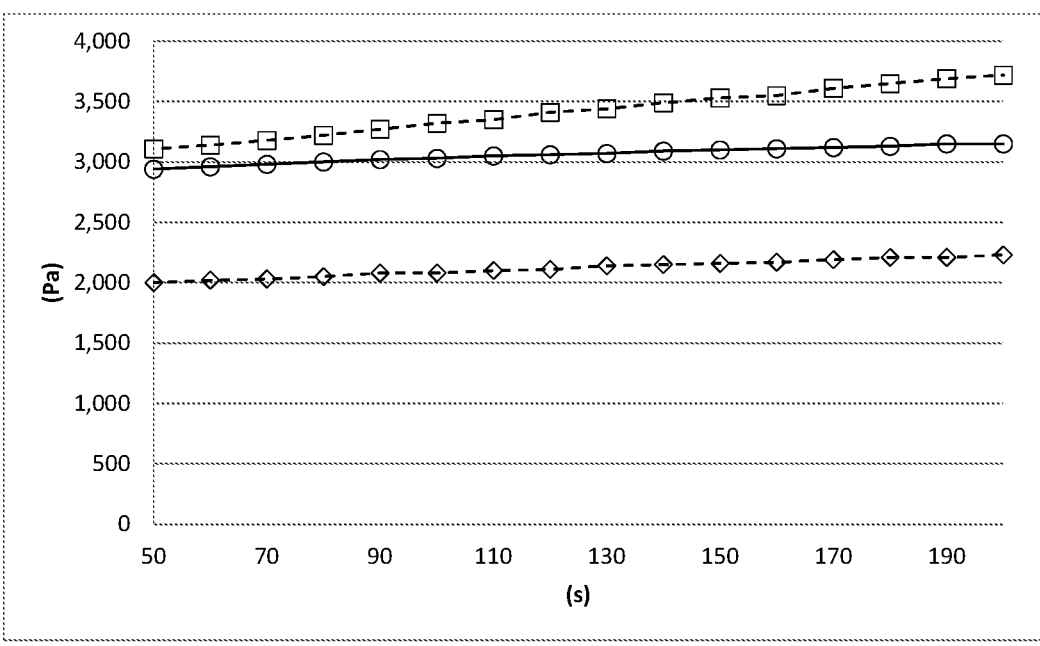

FIG. 1B shows that the G' of the inventive composition is more stable in time, i.e. it increases less with time, than the G' of compositions containing one kind of oleosomes only.

Hence, the present invention provides a composition which may be easier to manufacture and having at the same time advantageous properties.

Example 11

Cocktails beverages comprising oleosomes were prepared as follows: Samples of individual oleosomes and of blends thereof obtained as presented above (see Sample Preparation at RM2), were adjusted to pH 3 and were used to make beverages having two concentrations of oleosomes, 4 wt % and 0.5 wt % relative to the weight of the beverage. From the beverage samples, the creaming/turbidity stability was visually monitored over time. Individual and the oleosome blends were placed into flat-bottomed cylindrical glass tubes (180×10 mm, 0.6 mm wall) and left at room temperature. After 24 h, photos were taken.

Figure 4:
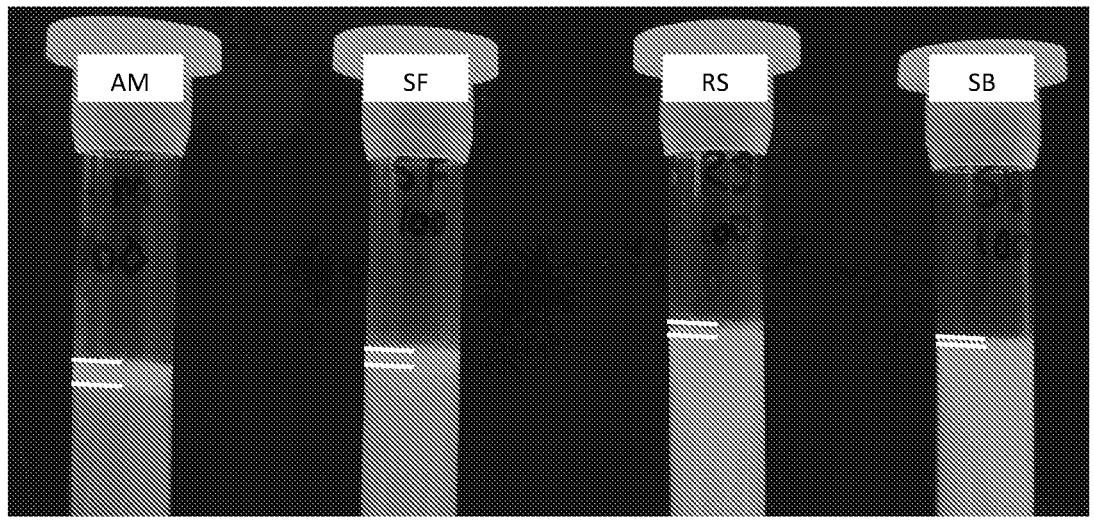
FIGS. 4 to 7 show the appearance of beverages containing a single kind of oleosomes compared with beverages containing the inventive composition.
Figure 5:
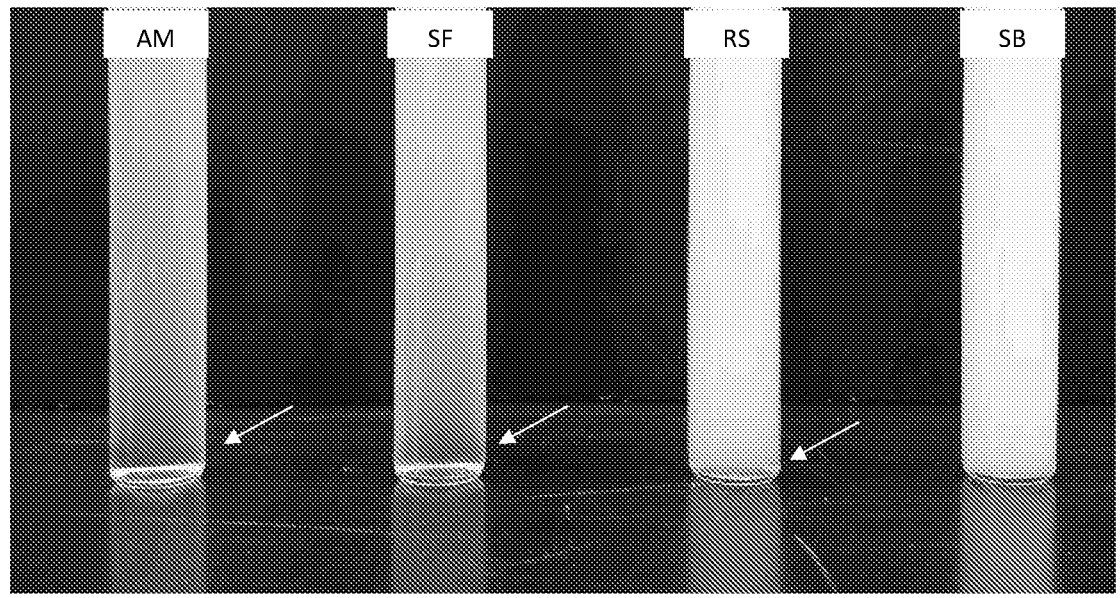

Differences can be observed among beverages containing individual oleosomes when looking at FIGS. 4 and 5. AM oleosomes presented the largest ring formation on top, followed by SF. Both RS and SB showed almost no ring formation (FIG. 4). Another observation is that AM and SF based beverages showed a depletion of the oleosomes at the bottom of the recipients containing thereof (i.e. they were clearer at the bottom than at the top), presenting a greater turbidity gradient when compared to beverages containing the RS and SB oleosomes (FIG. 5).

Figure 6:
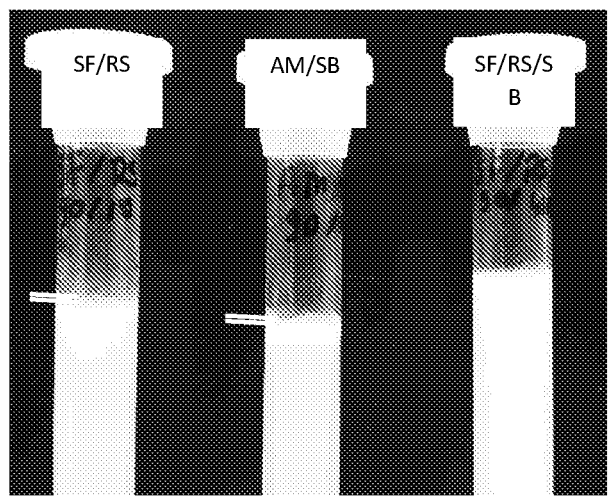
Figure 7:
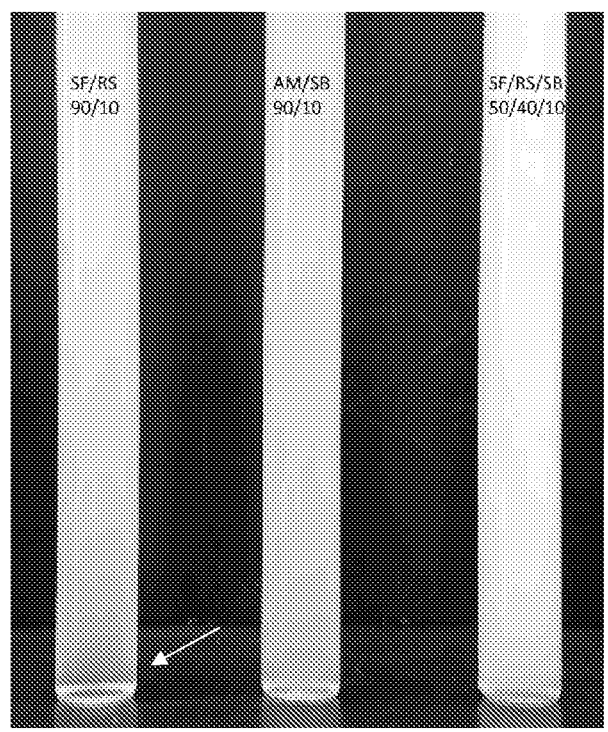

On the other hand, when blending 10 wt % of SB with 90 wt % AM (FIGS. 6 and 7), the ring formation and the clearing at the bottom was reduced. A similar outcome happened when blending 10% of RS with SF. The mixture of SF/RS/SB showed no ring formation and an improved and homogeneous turbidity which is a great advantage for cloudy beverages. Hence, the oleosome blends of the invention may be used to influence and tune clouding in beverage applications but also in other applications where such effect is desired. In addition, the advantage of using the blends of the invention is that the nutrition effect thereof was improved since the inventors were able to adjust the omega-3/omega-6 ratio. As well, the oleosome blends enabled a fine adjustment of the mouthfeel of the beverages which was considered excellent.

An additional improvement was in the taste of the various products containing the oleosome blends. For example the inventors observed that blending, reduces the unpleasant taste of certain oleosomes (e.g. soy) while improving the mouthfeel and other properties of said products. Also, the present invention allows the replacement oil bodies from sources which are on the allergy list with a blend of hypoallergenic oil bodies while the preferred properties, e.g. rheology, sensory, etc., of the initially used oleosomes can be preserved.

Examples 12 and 13

Lubricating products were made by dispersing oleosomes in water at a pH of 2.5 and a concentration of 0.5 wt % relative to the product's weight. A series of products was made by using almond (AM) and soybean (SB) individual oleosomes but also a blend thereof in a ratio 60 wt % AM and 40 wt % SB.

Another series was made by using sunflower (SF) and rapeseed (RS) individual oleosomes but also a blend thereof in a ratio 60 wt % SF and 40 wt % RS.

The lubricating properties of 1 mL aliquot samples were investigated following the procedure given below, by using an Anton Paar MCR 301 Controlled Stress Rheometer at 20° C. and a normal force-controlled (3N); tribology cell (T-PTD200/SOFT) with metal-elastomer tribo-pair (BC12.7-SN 9745 toolmaster detection); elastomer HTF8654_94/B100):

1. Segment 1 (non recording): temperature equilibration, 20° C., $F_N$=3N (hysteresis 0.02N), 2 minutes.
2. Segment 2 (recording): increasing deflection angle at very small oscillation amplitude; 20° C., $F_N$=3N (hysteresis 0.02N), deflection angle 1-100 mrad, 100 points of 6 seconds.
3. Segment 3 (non recording): rest; 20° C., $F_N$=3N (hysteresis 0.02N), 2 minutes.
4. Segment 4 (recording): constant speed; 20° C., $F_N$=3N (hysteresis 0.02N), speed 2.14 $min^{-1}$ (sliding speed 1.006 mm/s), 24 points (5 seconds, total time 120 seconds)

Figure 8A:
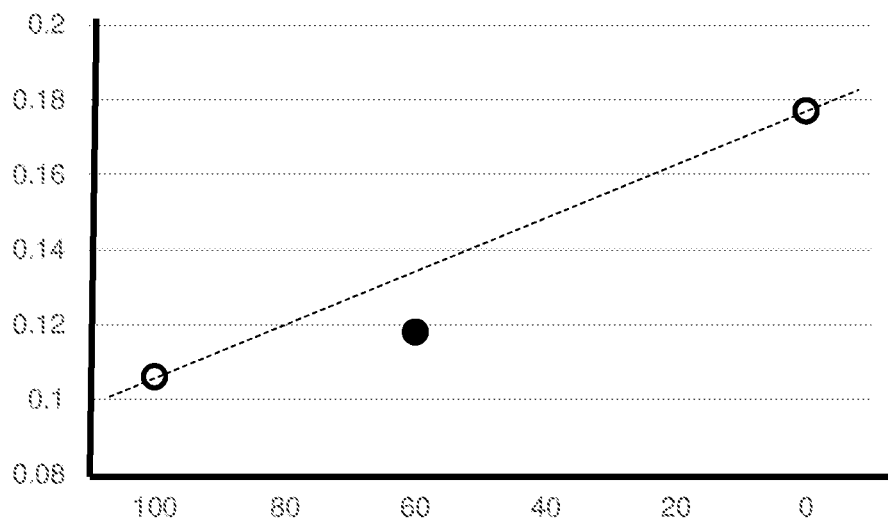
FIG. 8 show the friction properties of lubricating liquids containing a single kind of oleosomes compared with liquids containing the inventive composition.
Figure 8B:
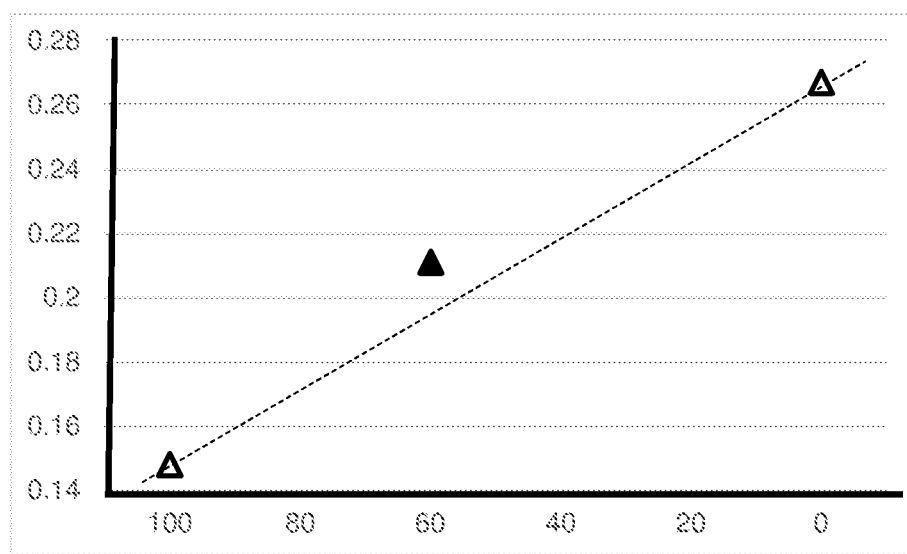

The results are presented in FIG. 8 showing the non-dimensional friction factor μ versus the oleosome composition. In FIG. 8A, 100 is corresponding to AM only containing sample and 0 to SB only containing sample. In FIG. 8B, 100 is corresponding to SF only containing sample and 0 to RS only containing sample. FIG. 8 demonstrates the synergistic behavior (i.e. the blend—filled circle/triangle—behaves differently than predicted—dotted line) of the oleosomes' blend and show the possibility of fine-tuning the lubricating behaviour of samples. As demonstrated in said figures, the inventors were able to fine tune the lubricating properties from values below those expected/predicted (FIG. 8A) to values above those expected/predicted (FIG. 8B). This demonstrates the flexibility of the invention in fine tuning the properties of products.

In short, by exploiting the invention, the inventors were able to:
i. provide products having an optimum ratio of Omega-3 to Omega-6 and hence improve the nutritional properties of products;
ii. mask unwanted flavours, enhance satiety and provide a solution for the addition of various naturally occurring vitamins (e.g. Vitamin E) without sacrificing the sensorial, rheological and other properties of products (and in fact enhancing them); and
iii. tune and most importantly, fine tune the properties of products to meet needs that couldn't have been met hitherto.

The invention claimed is:

1. A composition with reduced viscosity containing first oleosomes having a first size distribution D50(1) and second oleosomes having a second size distribution D50(2), wherein the first oleosomes are extracted from a source of origin which is different than the source of origin of said second oleosomes, wherein the first oleosomes are extracted from soy bean and the second oleosomes are extracted from almond, peanut, sunflower, coconut or sesame, wherein D50(1)<D50(2), and D50(1) is as most 550 nm and D50(2) is at most 6000 nm, wherein D50 is the diameter below which 50% of the volume of particles lie, and wherein the viscosity of the composition is reduced relative to viscosity of either the first oleosomes or the second oleosomes alone.

2. The composition of claim 1, wherein D50(1)/D50(2) is at least 0.001.

3. The composition of claim 1, wherein D50(1) is between 150 nm and 550 nm.

4. The composition of claim 1, wherein D50(2) is between 800 nm and 2500 nm.

5. The composition of claim 1, having a moisture content of at most 40 wt %.

6. A water-in-oil (W/O) or an oil-in-water (O/W) emulsion comprising the composition of claim 1.

7. A food and feed product, pharmaceutical product, personal care product or industrial product comprising the emulsion of claim 6.

8. A food and feed product, pharmaceutical product, personal care product and or industrial product comprising the composition of claim 1.

9. The composition of claim 1, having a moisture content of at most 30 wt %.

10. The composition of claim 1, having a moisture content of at most 20 wt %.

11. A composition with reduced viscosity comprising first oleosomes having a first size distribution D50(1) of at most 550 nm and second oleosomes having a second size distribution D50(2) of at most 6000 nm, wherein the first oleosomes are extracted from a source of origin which is different than the source of origin of said second oleosomes, wherein D50(1)<D50(2), and wherein the viscosity of the composition is reduced relative to viscosity of either the first oleosomes or the second oleosomes alone.

12. The composition of claim 11, wherein D50(1)/D50(2) is at least 0.001.

13. The composition of claim 11, wherein D50(1) is between 150 nm and 550 nm.

14. The composition of claim 11, wherein D50(2) is between 800 nm and 2500 nm.

15. The composition of claim 11, having a moisture content of at most 40 wt %.

16. A water-in-oil (W/O) or an oil-in-water (O/W) emulsion comprising the composition of claim 11.

17. A food and feed product, pharmaceutical product, personal care product or industrial product comprising the emulsion of claim 16.

18. A food and feed product, pharmaceutical product, personal care product and or industrial product comprising the composition of claim 1.

19. The composition of claim 11, having a moisture content of at most 30 wt %.

20. The composition of claim 11, wherein the oleosomes are extracted from members of Brassicaceae, Amaranthaceae, Asparagaceae, Echium, Glycine, Astaraceae, Fabaceae, Malvaceae, Faboidae, Aracaceae, Euphorbiceae, Sinapsis, Lamiaceae, Rosaceae, or Poaceae families.

* * * * *